United States Patent [19]
Hoffman et al.

[11] Patent Number: 4,876,366
[45] Date of Patent: Oct. 24, 1989

[54] ANTIHYPERCHOLESTEROLEMIC COMPOUNDS

[75] Inventors: William F. Hoffman; Ta J. Lee; Robert L. Smith, all of Lansdale; Clarence S. Rooney, Worcester, all of Pa.

[73] Assignee: Merck & Co., Inc., Rahway, N.J.

[21] Appl. No.: 205,407

[22] Filed: Jun. 10, 1988

Related U.S. Application Data

[63] Continuation-in-part of Ser. No. 859,534, May 5, 1986, abandoned.

[51] Int. Cl.$^4$ .................... A61K 31/365; C07D 309/30
[52] U.S. Cl. ..................................... 514/570; 549/292
[58] Field of Search ............... 549/292; 514/570, 824; 562/431, 496

[56] References Cited

U.S. PATENT DOCUMENTS 3,231,469  1/1966  Canonica ........................... 562/496
4,198,510  4/1980  Shioiri et al. ..................... 562/496
4,444,784  4/1984  Hoffman et al. ................... 549/292

FOREIGN PATENT DOCUMENTS 2022414 12/1979 United Kingdom ............... 514/570

Primary Examiner—Glennon H. Hollrah
Assistant Examiner—Ba Trinh
Attorney, Agent, or Firm—Melvin Winokur; Joseph F. DiPrima

[57] ABSTRACT

Novel 3-hydroxy-3-methylglutaryl-coenzyme A (HMG-CoA) reductase inhibitors which are useful as antihypercholesterolemic agents and are represented by the following general structural formulae (I) and (II):

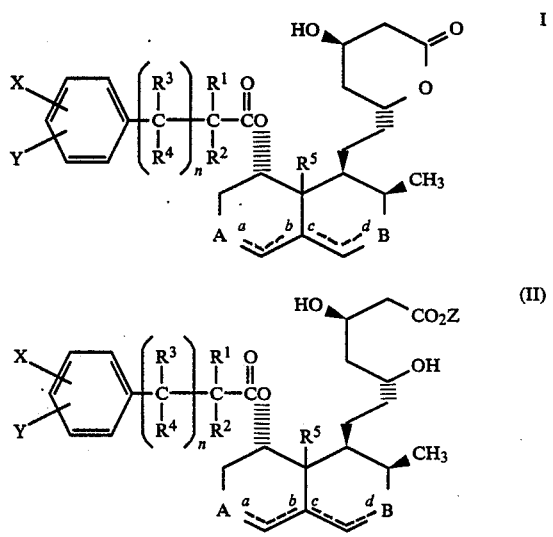

and pharmaceutically acceptable salts of the compounds (II) in which Z is hydrogen are disclosed.

22 Claims, No Drawings

ANTIHYPERCHOLESTEROLEMIC COMPOUNDS

This application is a continuation-in-part of Ser. No. 859,534 filed May 5, 1986 now abandoned.

BACKGROUND OF THE INVENTION

Hypercholesterolemia is known to be one of the prime risk factors for ischemic cardiovascular disease such as arteriosclerosis. To date, there is still no effective antihypercholesterolemic agent commercially available that has found wide patient acceptance. The bile acid sequestrants seem to be moderately effective but they must be consumed in large quantities, i.e. several grams at a time and they are not very palatable.

There are agents known, however, that are very active antihypercholesterolemic agents that function by limiting cholesterol biosynthesis by inhibiting the enzyme, HMG—CoA reductase. These agents include the natural fermentation products compactin and mevinolin and a variety of semi-synthetic and totally synthetic analogs thereof. The naturally occurring compounds and their semi-synthetic analogs have the following general structural formulae:

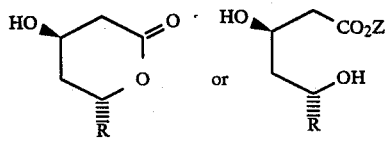

wherein:
Z is hydrogen, $C_{1-5}$ alkyl or $C_{1-5}$ alkyl substituted with a member of the group consisting of phenyl, dimethylamino, or acetylamino;
R is:

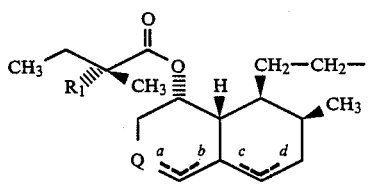

wherein
Q is

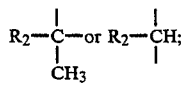

$R_2$ is H or OH;
$R_1$ is hydrogen or methyl; and a, b, c, and d represent optional double bonds, especially where b and d represent double bonds or a, b, c, and d are all single bonds.

U.S. Pat. No. 4,517,373 discloses semi-synthetic compounds represented by the above general formula wherein R is

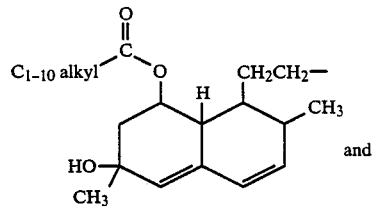

and

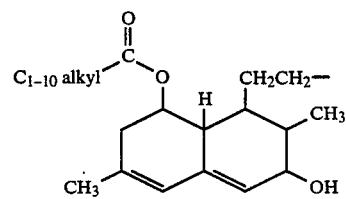

U.S. Pat. No. 4,346,227 and U.S. Pat. No. 4,448,979 also disclose semi-synthetic compounds represented by the above general formula wherein R is

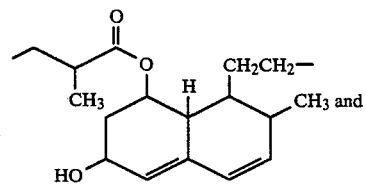

and

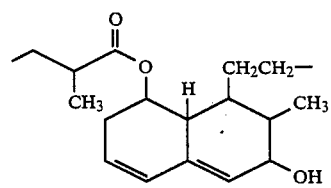

Japanese unexamined patent application No. J59-122,483-A discloses a semi-synthetic compound represented by the above general formula wherein R is

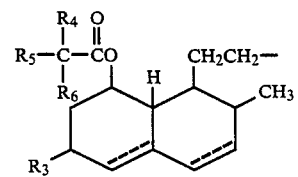

in which $R_3$ is hydrogen or methyl; $R_4$ is hydrogen, halogen or haloalkyl; $R_5$ is hydrogen, halogen or lower alkyl and $R_6$ is halogen, $N_3$, hydroxy, thio, amino, lower alkoxy, lower alkylthio and aralkylthio.

U.S. Pat. No. 4,444,784 discloses 8'-acyloxy derivatives of compactin, mevinolin and the dihydro and tetrahydro analogs thereof. Generically disclosed are the phenyl containing compounds represented by the above general formula wherein R is:

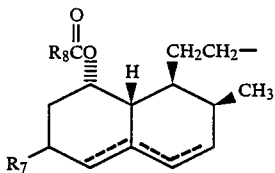

in which $R_7$ is hydrogen or methyl and $R_8$ is phenyl-$C_{1-3}$alkyl or substituted phenyl-$C_{1-3}$alkyl in which the substituent is halo, $C_{1-3}$alkyl or $C_{1-3}$alkoxy.

SUMMARY OF THE INVENTION

This invention relates to novel compounds which are HMG—CoA reductase inhibitors and are useful as antihypercholesterolemic agents. Specifically, the compounds of this invention are semi-synthetic analogs of compactin and mevinolin and the dihydro and tetrahydro analogs thereof which possess a specifically substituted 8'-ester acyl moiety. Additionally, pharmaceutical compositions of these novel compounds, as the sole therapeutically active ingredient, and in combination with bile acid sequestrants are disclosed.

DETAILED DESCRIPTION OF THE INVENTION

The specific HMG—CoA reductase inhibitors of this invention are the compounds represented by the following general structural formulae (I) and (II):

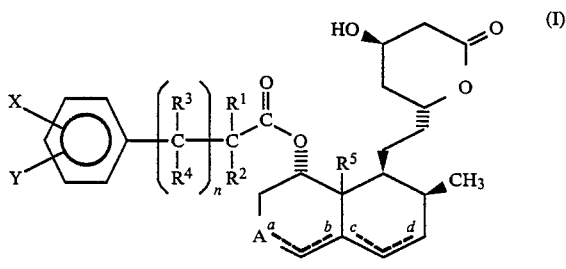
(I)

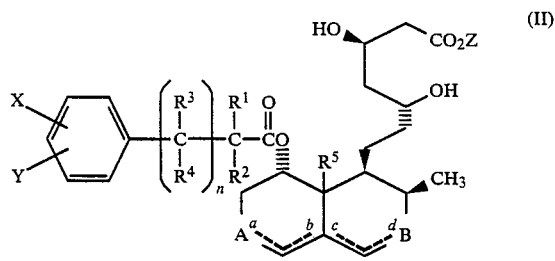
(II)

wherein:
n is 0 to 5;
$R^1$ is $C_{1-3}$alkyl;
$R^2$ is hydrogen or $C_{1-3}$alkyl;
$R^3$ and $R^4$ independently are hydrogen, $C_{1-3}$ alkyl, $C_{3-7}$ cycloalkyl, phenyl or substituted phenyl wherein the substituents are X and Y and when n is 2 to 5, each of the $R^3$s and $R^4$s are independently hydrogen, $C_{1-3}$alkyl, $C_{3-7}$cycloalkyl or only one of the $R^3$s and $R^4$s is phenyl or substituted phenyl;
$R^5$ is hydrogen or hydroxy;
X and Y independently are hydrogen, halogen (F, Cl or Br), trifluoromethyl, $C_{1-3}$ alkyl, nitro, cyano or a group selected from:

(a) $R^6O(CH_2)_m$ in which m is 0 to 3 and $R^6$ is hydrogen, $C_{1-3}$alkyl or hydroxy-$C_{1-3}$alkyl;
(b)

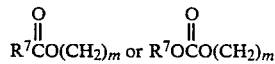

in which $R^7$ is hydrogen, $C_{1-3}$alkyl, hydroxyl-$C_{2-3}$alkyl, phenyl, naphthyl, amino-$C_{1-3}$alkyl, $C_{1-3}$alkylamino -$C_{1-3}$alkyl, di($C_{1-3}$alkyl)amino -$C_{1-3}$alkyl, hydroxy-$C_{2-3}$alkylamino -$C_{1-3}$alkyl or di(hydroxy-$C_{2-3}$-alkyl)amino-$C_{1-3}$alkyl;
(c)

in which $R^8$ is hydrogen, $C_{1-3}$alkyl, hydroxy-$C_{2-3}$alkyl, $C_{1-3}$alkoxy-$C_{1-3}$alkyl, phenyl or naphthyl;
(d) $R^9R^{10}N(CH_2)_m$,

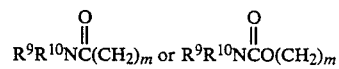

in which $R^9$ and $R^{10}$ independently are hydrogen, $C_{1-3}$alkyl, hydroxy-$C_{2-3}$alkyl or together with the nitrogen atom to which they are attached form a heterocyclic group selected from piperidinyl, pyrrolidinyl, piperazinyl, morpholinyl or thiomorpholinyl;
(e) $R^{11}S(O)_p(CH_2)_m$ in which p is 0 to 2 and $R^{11}$ is hydrogen, $C_{1-3}$alkyl, amino, $C_{1-3}$alkylamino or di($C_{1-3}$alkyl)amino;

A is

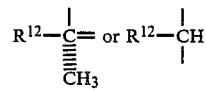

in which $R^{12}$ is hydrogen or hydroxy;
B is $CHR^{13}$ in which $R^{13}$ is hydrogen or hydroxy; and
a, b, c and d represent single bonds, one of a, b, c or d represents a double bond, both a and c or both b and d represent double bonds provided that when a is a double bond, A is

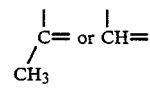

and when d is a double bond, B is

and
Z is hydrogen, $C_{1-5}$alkyl or $C_{1-5}$alkyl substituted with a member of the group consisting of phenyl, dimethylamino or acetylamino;
and pharmaceutically acceptable salts of the compounds of the formula (II) in which Z is hydrogen.

One embodiment of this invention is the class of compounds of the formulae (I) and (II) wherein $R^5$ is hydrogen, $R^{12}$ is hydrogen and $R^{13}$ is hydrogen and a, b, c, d represent single bonds or both b and d are double bonds.

Further illustrating this embodiment are those compounds represented by formula (I') and (II') wherein n is 0 to 2, and each $R^3$ and $R^4$ is selected from hydrogen or $C_{1-3}$alkyl; X and Y independently are hydrogen, halogen, hydroxy, $C_{1-3}$alkoxy, trifluoromethyl, $C_{1-3}$alkyl, methoxy, $C_{1-3}$alkyl, $C_{1-3}$alkylthiomethyl, hydroxymethyl and aminomethyl.

Preferably X and Y are hydrogen, halogen, trifluoromethyl, $C_{1-3}$alkyl, $C_{1-3}$alkoxy or hydroxy.

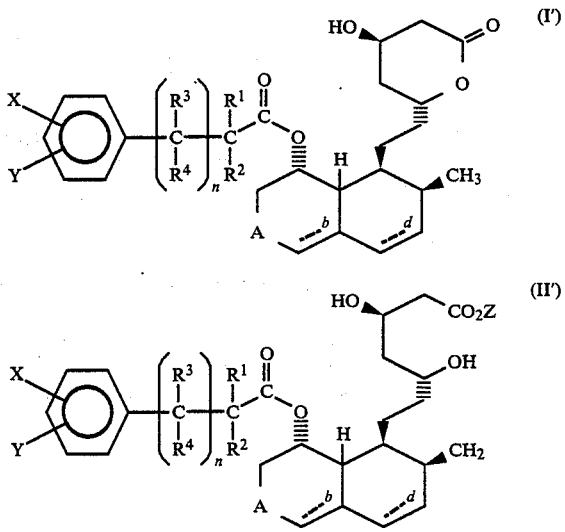

More specifically illustrating this embodiment are those compounds wherein $R^1$ is methyl, $R^2$ is methyl, and $R^3$ and $R^4$ are hydrogen. One subclass of this embodiment are the compounds of formula (I') wherein n is 0. Illustrative of this subclass are the following compounds:

(1) 6(R)-[2-[8(S)-(α,α-dimethylphenylacetyloxy)-2(S),6(R)-dimethyl-1,2,6,7,8,8a-(R)-hexadhydronaphthyl-1(S)]ethyl]-4(R)-hydroxy-3,4,5,6-tetrahydro-2H-pyran-2-one;

(2) 6(R)-[2-[8(S)-(α,α-dimethyl-4'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(3) 6(R)-[2-[8(S)-(α,α-dimethyl-3'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(4) 6(R)-[2-[8(S)-(α,α-dimethyl-4'-hydroxymethylphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(5) 6(R)-[2-[8(S)-(α,α-dimethyl-4'-hydroxy-3'-fluorophenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(6) 6(R)-[2-[8(S)-(α,α-dimethyl-4'-methoxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and (7) 6(R)-[2-[8(S)-(α,α-dimethyl-4'-ethoxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

A second subclass of this embodiment are the compounds of the formula (I') wherein n is 1. Representative of this subclass are the following compounds:

(1) 6(R)-[2-[8(S)-(α,α-dimethyl-3-phenylpropionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;

(2) 6(R)-[2-[8(S)-[α,α-dimethyl-3-(4'-hydroxyphenyl)-propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one; and (3) 6(R)-[2-[8(S)-[α,α-dimethyl-3-(3',5'-dihydroxyphenyl)-propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

A third subclass of this embodiment are the compounds of the formula (I') wherein n is 2. Representative of this subclass is the compound, 6(R)-[2-[8(S)-(α,α-dimethyl-4-phenylbutyryloxy)-2(S),6(R)-dimethyl-1,2,6,7,8,8a(R)-hexahydronaphthyl-1(S)ethyl]-4(R)-hydroxy-3,4,5,6-tetrahydro-2H-pyran-2-one.

Another embodiment of this invention is the class of compounds of the formula (II') wherein Z is hydrogen or $C_{1-5}$ alkyl and pharmaceutically acceptable salts of the compounds of the formula (II) wherein Z is hydrogen.

The pharmaceutically acceptable salts of this invention include those formed from cations such as sodium, potassium, aluminum, calcium, lithium, magnesium, zinc, and from bases such as ammonia, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide.

The compounds of formula (I) are conveniently prepared from compactin or mevinolin, or the appropriate dihydro or tetrahydro analog thereof via the following general synthetic pathway:

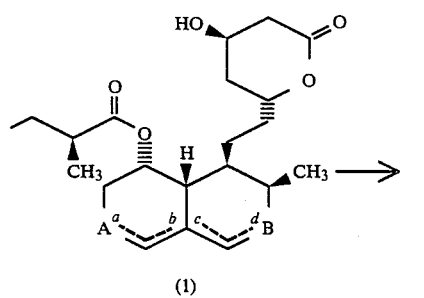

(1)

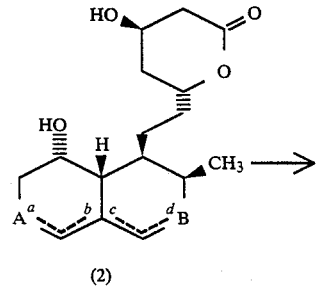

(2)

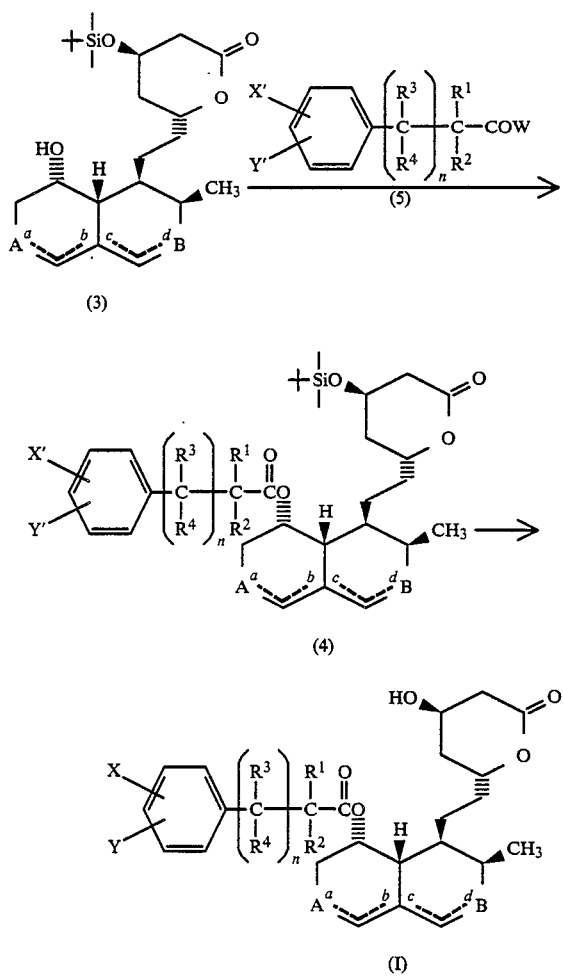

(3)

(4)

(I)

The starting materials compactin, mevinolin, and their dihydro and tetrahydro analogs are readily available or may be prepared according to fermentation procedures disclosed in U.S. Pat. No. 3,983,140, U.S. Pat. No. 4,049,495, U.S. Pat. No. 4,231,938, U.S. Pat. No. 4,294,846, and U.S. Pat. No. 4,343,814, and the hydrogenation procedures disclosed in U.S. Pat. No. 4,351,844. The appropriate starting material of formula (1) is then hydrolyzed under the conditions disclosed in U.S. Pat. No. 4,444,784 to afford the compounds of formula (2). The 4-hydroxy function in the lactone moiety of the compounds of formula (2) is protected with a suitable protecting agent, exemplified here as a dimethyl-t-butylsilyl group, according to the procedure disclosed in U.S. Pat. No. 4,444,784. Acylation of the 8' hydroxy group of the compounds of the formula (3) is accomplished under suitable conditions utilizing the appropriately substituted acids or acid halides of the formula (5) wherein n, $R^1$, $R^2$, $R^3$ and $R^4$ are as described above, X' and Y' are X and Y respectively as described above except that when X or Y contains a hydroxyl group that group is protected with a suitable protecting group, such as a dimethyl-t-butylsilyl group and W is hydroxy, bromo or chloro. The protecting groups of the compound of formula (4) are removed utilizing suitable conditions to afford the compounds of the formula (I). For the compounds of this invention wherein the polyhydronaphthyl moiety is substituted with a hydroxy group, the compound of the formula (4) is subject to a microbiological hydroxylation after the removal of the protecting groups utilizing the general procedures disclosed in U.S. Pat. No. 4,346,227, U.S. Pat. No. 4,448,979, U.S. Pat. No. 4,517,373 and Japanese patent application No. J-60-130,548.

The appropriately substituted acids or acid halides of the formula (5) are commercially available or prepared from known starting materials utilizing standard chemical transformations.

One sequence to alkyl substituted carboxylic acids follows the method employed by Reetz et al., Chem. Ber., 116, 3708 (1983). This route, involves the addition of tertiary alkyl halides to a ketene silyl acetal

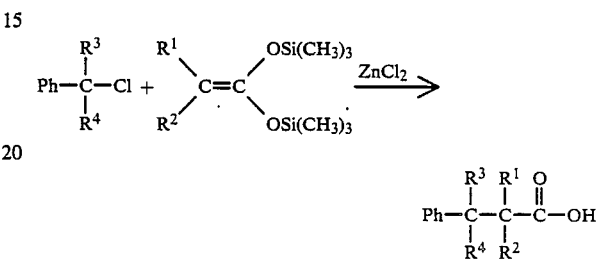

in the presence of $ZnCl_2$. Methodology leading to tertiary phenyl or substituted phenylalkyl halides is well known in the organic literature as exemplified by H. C. Brown et al., J. Am. Chem. Soc., 90 2082 (1968) and G. A. Olah, J. Am. Chem. Soc., 91, 1458 (1969). Substituents on the phenyl ring, such as hydroxy, which may be effected by transformations, such as the Grignard reaction, should be protected following methodology in Greene, Protective Groups In Organic Synthesis, J. Wiley (1981).

Less sterically hindered carboxylic acids may be prepared, by reaction of an appropriate phenyl alkyl halide with isobutyric acid or propanoic acid following Example 4. Aldehydes and ketones may also serve as electrophiles following the lithium anion chemistry of Example 4(a); in this case, the resultant alcohol would be removed by dehydration or by conversion to the ketone followed by a Wolff-Kisher or Clemmsen reduction methodology.

The compounds of the formula (II) wherein Z is hydrogen or a pharmaceutically acceptable salt thereof are readily prepared by the mild basic hydrolysis of the lactone moiety of the compounds of formula (I), careful acidification and formation of the appropriate salt utilizing standard procedures.

The compounds of the formula (II) wherein Z is $C_{1-5}$ alkyl or a substituted $C_{1-5}$ alkyl may be conveniently prepared by the procedures described in U.S. Pat. No. 4,342,767.

The compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 2 mg to 2000 mg (preferably 10 to 100 mg) which may be given in two to four divided doses. Higher doses may be favorably employed as required.

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)iminotrimethylene dihalide]. The relative amounts of the compounds of this invention and these polymers is between 1:100 and 1:15,000.

The intrinsic HMG—CoA reductase inhibition activity of the claimed compounds is measured in the in vitro protocol published in *J. Med. Chem.*, 28, p. 347-358 (1985) and described below:

ISOLATION OF HMG—CoA REDUCTASE

Male Holtzman Sprague-Dawley rats (225–250 g) were kept on reversed lighting and fed Purina rat chow containing 3% cholestyramine for 7 days preceding their sacrifice by $CO_2$ asphyxiation. Livers were removed 6 hours into the dark cycle and used immediately to prepare microsomes. HMG—CoA reductase was solubilized from the freshly prepared microsome by the method of Heller and Shrewsbury [*J. Biol. Chem.*, 1976, 251, 3815] and purified through the the second ammonium sulfate precipitation step as described by Kleinsek et al. [*Proc. Natl. Acad. Sci. USA*, 1977, 74, 1431]. The enzyme preparation was tested for HMG—CoA reductase potency and diluted with 100 mM phosphate buffer (pH 7.2) so that 100 μl of the enzyme solution, when added to the assay control, gave a value of 50,000–60,000 dpm. The enzyme preparation was stored at −80° C.

HMG—CoA REDUCTASE INHIBITION ASSAY

The assay is essentially the procedure of Shefer et al. [*J. Lipid Res.*, 1972, 13, 402]. The complete assay medium contained the following in a total volume of 0.8 ml: phosphate buffer, pH 7.2, 100 mM; $MgCl_2$, 3 mM; NADP, 3 mM; glucose 6-phosphate, 10 mM; glucose-6-phosphate dehydrogenase, 3 enzyme units; reduced glutathione, 50 mM; HMG—CoA (glutaryl-3-$^{14}$C, New England Nuclear), 0.2 mM (0.1 μCi); and partially purified enzyme stock solution, 100 μL.

Test compounds or compactin (after first being converted to the sodium salt of their dihydroxy acid form in situ by addition of 1N NaOH (1 equivalent) were added to the assay system in 10-μL volumes at multiconcentration levels. After a 40-minute incubation at 37° C. with shaking and exposure to air, the reaction was stopped by the addition of 0.4 mL of 8N HCl. After an additional 30-minute incubation period at 37° C. to ensure the complete lactonization of mevalonic acid to mevalonolactone, 0.2 ml of the mixture was added to an 0.5×5.0 cm column containing 100–200 mesh Bio-Rex 5, chloride form (Bio-Rad), wetted with distilled water, as described by Alberts et al [*J. Proc. Natl. Acad. Sci. U.S.A.*, 1980, 77, 3967]. The unreacted [$^{14}$C]HMG—CoA was absorbed on the resin and the [$^{14}$C]mevalonolactone was eluted with distilled water (2×1 ml) directly into 7-ml scintillation vials. Five milliliters of Aquasol-2 (New England Nuclear) was added to each vial, and radioactivity was measured in a Packard Tri Carb Prias scintillation counter. $IC_{50}$ values were determined by plotting percentage inhibition against test compound concentration and fitting a straight line to the resulting data by using the least-squares method. For estimation of relative inhibitory potencies, compactin was assigned a value of 100 and the $IC_{50}$ value of the test compound was compared with that of compactin determined simultaneously.

Representative of the intrinsic HMG—CoA reductase inhibitory activities of the claimed compounds tabulated below for a number of the claimed compounds are the relative potencies for said compounds.

TABLE 1

| T | Relative Potency[1] |
|---|---|
| phenyl-C(CH₃)₂– | 88 |
| 4-HO-phenyl-C(CH₃)₂– | 217 |
| 3-HO-phenyl-C(CH₃)₂– | 197 |
| phenyl-CH₂C(CH₃)₂– | 173 |
| 4-CH₃O-phenyl-C(CH₃)₂– | 144 |
| 4-HOCH₂-phenyl-C(CH₃)₂– | 36 |
| 4-HO-3-F-phenyl-C(CH₃)₂– | 217 |

TABLE 1-continued

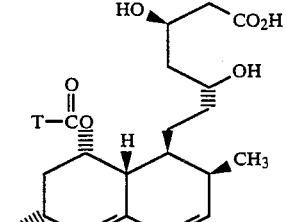

| T | Relative Potency[1] |
|---|---|
| 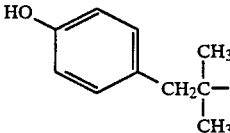 | 280 |
| 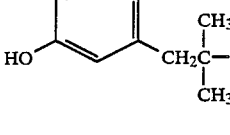 | 333 |
| 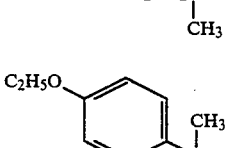 | 100 |
| (C₂H₅O-phenyl-C(CH₃)₂-) | 47 |

[1]Relative to compactin arbitrarily assigned a value of 100

Included within the scope of this invention is the method of treating arteriosclerosis, familial hypercholesterolemia or hyperlipidemia which comprises administering to a subject in need of such treatment a nontoxic therapeutically effective amount of the compounds of formulae (I) or (II) or pharmaceutical compositions thereof.

The following examples illustrate the preparation of the compounds of the formulae (I) and (II) and their incorporation into pharmaceutical compositions and as such are not to be considered as limiting the invention set forth in the claims appended hereto.

EXAMPLE 1

Preparation of
6(R)-[2-[8(S)-(α,α-Dimethyl-4'-hydroxy-phenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) 2-(4-(Dimethyl-tert-butylsilyloxy)phenyl)propionic acid (1a)

Into dry tetrahydrofuran (20 ml) at 0° C. under anhydrous conditions was added slowly with stirring lithium diisopropylamide (2.67 g, 25 mmol) and then a solution of 4-(dimethyl-tert-butylsilyloxy)phenylacetic acid (2.66 g, 10 mmoles) in tetrahydrofuran (10 ml) was added dropwise. The resultant brown solution was stirred at 20°-25° C. for one hour and at 50° C. for 30 minutes. The solution was then cooled to 0° C. and methyl iodide (3.54 g, 25 mmol) was added dropwise. The reaction mixture was stirred at ambient temperature for about 16 hours and then quenched with saturated aqueous ammonium chloride (20 ml) and acidified with 3N hydrochloric acid. The reaction mixture was extracted with diethyl ether (3×100 ml) and the combined extracts washed with saturated aqueous sodium chloride (2×50 ml), dried over magnesium sulfate and the solvent removed in vacuo to afford a tan oil. The oil was chromatographed on a 5×15 cm column of silica gel eluted with 10 percent isopropanol/hexane to yield the desired product as a solid. m.p. 52°-4° C.

Anal. Calc'd for $C_{15}H_{24}O_3Si$: C, 64.24; H, 8.62. Found: C, 64.25; H, 8.55.

(b) 2-[4-(Dimethyl-tert-butylsilyloxy)phenyl]-2-methylpropionic acid (1b)

Distilled diisopropylamine (1.98 g, 19.6 mmol) was added to dry tetrahydrofuran (10 ml) under anhydrous conditions. To the stirred solution at 0° C. was added 1.55M n-butyllithium (12.6 ml, 19.6 mmol) in hexane dropwise. After 15 minutes a solution of the compound (1a) (2.2 g, 7.8 mmole) in tetrahydrofuran (10 ml) was added dropwise at 0° C. The reaction mixture was stirred for 1 hour at ambient temperature 30 minutes at 50° C. and then cooled to 0° C. Methyl iodide (2.78 g, 19.6 mmol) was added dropwise, and the reaction mixture stirred at ambient temperature for about 16 hours. The reaction was quenched with saturated ammonium chloride (20 ml) and acidified with 3N hydrochloric acid. The reaction mixture was extracted with diethyl ether (3×100 ml), the extracts combined, washed with saturated aqueous sodium chloride, dried over magnesium sulfate and concentrated in vacuo to give a tan solid. This compound was chromatographed on a 5×15 cm column of silica gel eluted with 5 percent isopropanol/hexane to yield the desired product as a solid, m.p. 78-80° C.

Anal. Calc'd for $C_{16}H_{26}O_3Si$: C, 65.26; H, 8.90. Found: C, 65.44; H, 9.08.

(c) 6(R)-[2-[8(S)-[α,α-Dimethyl-4'-(dimethyl-tert-butylsilyloxy)phenylacetyloxy]-2(S),6(R)-dimethyl-1,2,6,7,8,8a(R)hexahydronaphthyl-1(S)]ethyl]-4(R)-(dimethyl-ert-butylsilyloxy)-3,4,5,6-tetrahydro-2H-pyran-2-one To a solution of the compound (1b) (1.08 g, 2.5 mmol) and N-methylmorpholine (550 μl, 5 mmole) in methylene chloride (20 ml) at −5° C. was added dropwise 2,4-dichloro-6-methoxytriazine (0.9 g, 5 mmol) dissolved in methylene chloride (10 ml) and reaction mixture was stirred for 1.5 hours at −5° to 0° C. To the reaction mixture was added dropwise 6(R)-[2-[8(S)-hydroxy-2(S),6(R)-dimethyl-1,2,6,7,8,8a(R)-hexahydronaphthyl-1(S)]ethyl]-4(R)-dimethyl-tert-butylsilyloxy-3,4,5,6-tetrahydro-2H-pyran-2-one (1.08 g, 2.5 mmol) [see U.S. Pat. No. 4,444,784] in methylene chloride (10 ml). The reaction mixture was refluxed for three days. The reaction mixture was then cooled and poured into diethyl ether (200 ml) and the reaction mixture washed with water (25 ml), 1N hydrochloric acid (15 ml) and saturated aqueous sodium chloride, dried over magnesium sulfate and evaporated in vacuo to give an orange oil. The oil was chromatographed on a 5×15 cm column of silica gel eluted with methylene chloride to give the desired product as a glassy solid.

(d) 6(R)-[2-[8(S)-(α,α-Dimethyl-4'-hydroxy-phenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one The compound (1c) (0.3 g, 0.42 mmol) was dissolved in tetrahydrofuran (50 ml). To the solution under nitrogen was added glacial acetic acid (0.2 g, 3.37 mmol) and 1M tetrabutylammonium fluoride (2.53 ml, 2.5 mmol) in tetrahydrofuran. The mixture was stirred at ambient temperature for about 16 hours and then concentrated in vacuo. The residue was partitioned between water (50 ml) and diethyl ether (100 ml). The aqueous phase was extracted with diethyl ether (100 ml). The diethyl ether phases were combined, washed with 1N hydrochloric acid (10 ml) and saturated aqueous sodium chloride (2×25 ml) and then dried over magnesium sulfate and concentrated in vacuo to give a viscous yellow oil. The oil was chromatographed on a 4×15 cm column of silica gel eluted with 20 percent acetone/methylene chloride (1 L) and then 25 percent acetone/methyl chloride to give a viscous oil which was triturated with hexane to afford an amorphous solid.

Anal. Calc'd for $C_{25}H_{38}O_6 \cdot 0.25H_2O$: C, 71.50; H, 7.97. Found: C, 71.45; H, 8.12.

EXAMPLE 2

Preparation of 6(R)-[2-[8(S)-(α,α-Dimethylphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) 6(R)-[2-[8(S)-(α,α-Dimethylphenylacetyloxy)-2(S),6(R)-dimethyl-1,2,6,7,8,8a(R)-hexahydronaphthyl-1(S)]ethyl]-4(R)-(dimethyl-tert-butylsilyloxy)-3,4,5,6-tetrahydro-2H-pyran-2-one (2a)

Utilizing the general procedure of Example 1(c) 6(R)-[2-[8(S)-hydroxy-2(S),6(R)-dimethyl-1,2,6,7,8,8a(R)-hexahydronaphthyl-1(S)]ethyl]-4(R)-(dimethyl-tert-butylsilyloxy)-3,4,5,6-tetrahydro-2H-pyran-2-one (1.08 g, 2.5 mmol) and α,α-dimethylphenylacetic acid (0.82 g, 5.0 mmol) were reacted to afford the desired product as a viscous oil.

(b) 6(R)-[2-[8(S)-(α,α-Dimethylphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Utilizing the general procedure of Example 1(d) the compound (2a) (0.42 g, 0.72 mmol) was converted into the desired product as a white solid m.p. 68°–70° C.

Anal. Calc'd for $C_{29}H_{38}O_5$: C, 74.65; H, 8.21. Found: C, 74.74; H, 8.52.

EXAMPLE 3

Preparation of 6(R)-[2-[8(S)-(α,α-Dimethyl-3'-hydroxy-phenylacetyloxy)-2(S),6(R)-dimethyl-1,2,6,7,8,8a(R)-tetrahydronaphthyl-1(S)]ethyl]-4(R)-hydroxy-3,4,5,6-tetrahydro-2H-pyran-2-one (a) (3-Dimethyl-tert-butylsilyloxyphenyl)acetic acid (3a)

To a stirred solution of 3-hydroxyphenylacetic acid (7.6 g, 50 mmol) in dimethylformamide (50 ml) was added dimethyl-tert-butylsilylchloride (16.6 g, 110 mmol) and imidazole (15.0 g, 220 mmol) at ambient temperature under nitrogen. The reaction mixture was stirred about 16 hours and then poured into diethyl ether (500 ml). The resulting mixture was washed with water (200 ml) and the aqueous phase extracted with diethyl ether (100 ml). The organic layer and the diethyl ether extract were combined, washed with 3N hydrochloric acid (50 ml) and saturated aqueous sodium chloride (2×100 ml), dried over magnesium sulfate and concentrated in vacuo to give a yellow oil. To a solution of the oil in methanol (50 ml) was added slowly a solution of potassium carbonate (97.6 g, 55 mmol) in water (50 ml). The resulting solution was stirred for 1 hour at ambient temperature and then acidified to pH 3 with 1M potassium bisulfate. The mixture was extracted with diethyl ether (3×100). The combined extracts were washed with saturated aqueous sodium chloride (2×50) ml), dried over magnesium sulfate and concentrated in vacuo. The desired product was purified by distillation b.p. 142° C./0.4 mmHg.

Anal. Calc'd for $C_{14}H_{22}O_3Si$: C, 63.11; H, 8.32. Found: C, 62.80; H, 8.22.

(b) 2-[3-(Dimethyl-tert-butylsilyloxy)phenyl]-2-methylpropionic acid (3b)

Utilizing the general procedures of Examples 1(a) and 1(b), the compound (3a) (2.66 g, 10 mmol) was converted into the desired product as a pale yellow solid, m.p. 72°–4° C.

Anal. Calc'd for $C_{16}H_{26}O_3Si$: C, 65.26; H, 8.96. Found: C, 65.36; H, 9.13.

(c) 6(R)-[2-[8(S)-([α,α-Dimethyl-3'-(tert-butyldimethylsilyoxy)phenylacetyloxy]-2(S),6(R)-dimethyl-1,2,6,7,8,8a(R)-hexahydronaphthyl-1(S)]ethyl]-4(R)-(tert-butyldimethylsilyloxy)-3,4,5,6-tetrahydro-2H-pyran-2-one Utilizing the general procedure of Example 1(c), 6(R)-[2-[8(S)-hydroxy-2(S),6(R)-dimethyl-1,2,6,7,8,8a(R)-hexahydronaphthyl-1(S)]ethyl]-4(R)-(dimethyl-tert-butylsilyloxy)-3,4,5,6-tetrahydro-2H-pyran-2H-one (1.08 g, 2.5 mmol) and the compound (3b) (1.47 g, 25 mmol) were reacted to afford the desired product as a rose colored viscous oil.

NMR (CDCl₃) δ=0.10 (6H, s), 0.17 (6H, s), 0.71 (3H, d, J=7 Hz), 0.83 (3H, d, J=7 Hz), 0.90 (9H, s), 0.97 (9H, s), 1.53 (3H, s), 1.56 (3H, 3), 4.28 (H, m), 4.49 (H, m), 5.30 (H, m), 5.41 (H, m), 5.75 (H, dd, J=6 Hz, 10 Hz), 5.95 (H, d, J=10 Hz), 6.66 (H, d, J=9 Hz), 6.86 (H, s), 6.95 (H, d, J=9 Hz), 7.11 (H, m).

(d)
6(R)-[2-[8(S)-(α,α-Dimethyl-3'-hydroxy-phenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one Utilizing the general procedure of Example 1(d), the compound (3c) (0.34 g, 0.478 mmol) was converted into the desired product as a colorless solid m.p. 154°–7° C.
Anal. Calc'd for $C_{29}H_{38}O_6$: C, 72.17; H, 7.94. Found: C, 71.88; H, 8.19.

EXAMPLE 4

Preparation of 6(R)-[2-[8(S)-(α,α-Dimethyl-3-phenyl-propionyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (a) 2,2-Dimethyl-3-phenylpropionic acid (4a)

To a stirred solution of diisopropylamine (12.6 g, 125 mmol) in tetrahydrofuran (100 ml) under anhydrous conditions at 0° C. was added n-butyllithium (80.6 ml, 1.55M in hexane, 125 mmol). The reaction mixture was stirred for 30 minutes at 5° C. and then isobutyric acid (4.4 g, 50 mmol) was added. The reaction mixture was stirred at 0° C. for 30 minutes and then benzyl bromide (17.1 g, 100 mmol) was added dropwise. The reaction mixture was stirred for 2 hours at ambient temperature, quenched with saturated aqueous ammonium chloride (60 ml) and then acidified with 6N hydrochloric acid with cooling. The aqueous phase was saturated with sodium chloride and extracted with diethyl ether (2×100 ml). The combined organic phase was washed with saturated aqueous sodium chloride (2×25 ml) and then dried over magnesium sulfate and concentrated in vacuo to give viscous oil. The oil was distilled at 0.2 mmHg and the product was collected at 160°–170° C. The product was purified by chromatography on a 5×15 cm column of silica gel eluted with 10 percent diethyl ether/hexane (1 L) and 50 percent diethyl ether/hexane (1 L) to afford the desired product as a colorless solid. m.p. 58°–9° C.

NMR (CDCl₃) δ=1.21 (6H, s), 2.90 (2H, s), 7.15–7.28 (5H, m).

(b)
6(R)-[2-[8(S)-(α,α-Dimethyl-3-phenylpropionyloxy)-2(S),6(R)-dimethyl-1,2,6,7,8,8a(R)-hexahydronaphthyl-1(S)]ethyl]-4(R)-tert-butyldimethylsilyloxy)-3,4,5,6-tetrahydro-2H-pyran-2-one Utilizing the general procedure of Example 1(c), 6(R)-[2-[8(S)-hydroxy-2(S),6(R)-dimethyl-1,2,6,7,8,8a(R)-hexahydronaphthyl-1(S)]ethyl]-4(R)-dimethyl-tert-butylsilyloxy-3,4,5,6-tetrahydro-2H-pyran-2-one (1.08 g, 2.5 mmol) and the compound (4a) (0.89 g, 50 mmol) were reacted to afford the desired product as a viscous oil.

NMR (CDCl₃) δ=0.07 (6H, s), 0.87 (9H, s), 4.29 (H, m), 4.58 (6H, m), 5.38 (H, m), 5.48 (H, m), 5.76 (H, dd, J=6 Hz, 10 Hz), 5.98 (H, d, J=10 Hz), 7.12–7.27 (5H, m).

(c)
6(R)-[2-[8(S)-(α,α-Dimethyl-3-phenylpropionyloxy)-2(S),6(R)-dimethyl-1,2,6,7,8,8a(R)-hexahydronaphthyl-1(S)]ethyl]-4(R)-hydroxy-3,4,5,6-tetrahyro-2H-pyran-2-one Utilizing the general procedure of Example 1(d), the compound (4b) (0.46 g, 0.77 mmol) was converted into the desired product as an amorphous solid.
Anal. Calc'd for $C_{30}H_{40}O_5$: C, 74.97; H, 8.39. Found: C, 75.21; H, 8.61.

EXAMPLE 5

Preparation of 6(R)-[2-[8(S)-(α,α-Dimethyl-4'-methoxy-phenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H -pyran-2-one To a stirred solution of 6(R)-[2-[8(S)-(α,α-dimethyl-4'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (48.7 mg, 0.1 mmol) in dimethylformamide (5 ml) was added potassium carbonate (13.8 mg, 0.1 mmol) and the reaction mixture stirred for 30 minutes at ambient temperature. To the reaction mixture was then added methyl iodide (28.4 mg, 0.2 mmol) and the reaction mixture was stirred at ambient temperature for 7 hours. The reaction mixture was poured into diethyl ether (100 ml) and washed with water (2×10 ml). The diethyl ether phase was dried over magnesium sulfate and concentrated in vacuo to a viscous yellow oil. The oil was chromatographed on a 3×15 cm column of silica gel eluted with 10 percent acetone:methylene chloride (500 ml) and then 15 percent acetone:methylene chloride (500 ml) to yield the desired product as an amorphous solid.
Anal. Calc'd for $C_{30}H_{40}O_6$: C, 72.55; H, 8.12. Found: C, 72.60; H, 8.50.

EXAMPLES 6 TO 11

Utilizing the general procedures of Example 1, the following compounds were prepared from the appropriately substituted acid or acid chloride and 6(R)-[2-[8(S)-hydroxy-2(S),6(R)-dimethyl-1,2,6,7,8,8a(R)-hexahydronaphthyl-1(S)]ethyl]-4(R)-(dimethyl-tert-butyl-silyloxy)-3,4,5,6-tetrahydro-2H-pyran-2-one.

TABLE 2

| Compound No. | |
|---|---|
| 6 | 6(R)-[2-[8(S)—(α,α-Dimethyl-4'-hydroxy-methylphenylacetyloxy)-2(S),6(R)-dimethyl-1,2,6,7,8,8a(R)-hexahydronaphthyl-1(S)]—ethyl]-4(R)-hydroxy-3,4,5,6-tetrahydro-2H—pyran-2-one<br>Anal. Calc'd for $C_{30}H_{40}O_6 \cdot \frac{1}{4}H_2O$: C, 71.90; H, 8.15.<br>Found C, 71.79; H, 8.27. |
| 7 | 6(R)-[2-[8(S)—(α,α-Dimethyl-4'-hydroxy-3'-fluorophenylacetyloxy)-2(S),6(R)-dimethyl-1,2,6,7,8,8a(R)-hexahydronaphthyl-1(S)]—ethyl]-4(R)-hydroxy-3,4,5,6-tetrahydro-2H-pyran-2-one<br>Anal. Calc'd for $C_{29}H_{37}FO_6 \cdot 0.2CH_2Cl_2$: C, 67.75; H, 7.28.<br>Found C, 67.67; H, 7.32. |
| 8 | 6(R)-[2-[8(S)—(α,α-Dimethyl-4'-ethoxy-phenylacetyloxy)-2(S),6(R)-dimethyl-1,2,6,7,8,8a(R)-hexahydronaphthyl-1(S)]—ethyl]-4(R)-hydroxy-3,4,5,6-tetrahydro-2H—pyran-2-one<br>Anal. Calc'd for $C_{31}H_{42}O_6 \cdot \frac{1}{4}H_2O$; |

TABLE 2-continued

| Compound No. | |
|---|---|
| | C, 72.27; H, 8.32.<br>Found C, 72.17; H, 8.54. |
| 9 | 6(R)-[2-[8(S)—(α,α-Dimethyl-3-(4'-hydroxylphenyl)-propionyloxy)-2(S),6(R)-dimethyl-1,2,6,7,8,8a(R)-hexahydronaphthyl-1(S)]ethyl]-4(R)-hydroxy 3,4,5,6-tetrahydro-2H—pyran-2-one<br>Anal. Calc'd for $C_{30}H_{40}O_6 \cdot \frac{1}{4}C_4H_{10}O$:<br>C, 72.27; H, 8.32.<br>Found C, 71.96; H, 8.31. |
| 10 | 6(R)-[2 [8(S)—[(α,α-Dimethyl-3-(3',5'dihydroxyphenyl)-propionyloxy]-2(S),6(R)-dimethyl-1,2,6,7,8,8a(R) hexahydronaphthyl-1(S)]ethyl]-4(R)-hydroxy-3,4,5,6-tetrahydro-2H—pyran-2-one<br>Anal. Calc'd for<br>C, 65.99; H, 7.44.<br>Found C, 66.33; H, 7.29. |
| 11 | 6(R)-[2-[8(S)—(α,α-Dimethyl-4-phenyl-butyryloxy)-2(S),6(R)-dimethyl-1,2,6,7,8,8a-(R)-hexahydronaphthyl-1(S)]ethyl]-4(R)-hydroxy-3,4,5,6-tetrahydro-2H-pyran-2-one<br>Mp 157-90° C.<br>Anal. Calc'd for $C_{31}H_{42}O_5$;<br>C, 75.27; H, 8.56.<br>Found C, 75.21; H, 8.76. |

EXAMPLES 12 TO 20

Utilizing the general procedures of Example 1, the following compounds are prepared from the appropriately substituted acid or acid chloride and compactin, mevinolin and the dihydro and tetrahydro analogs thereof.

TABLE 3

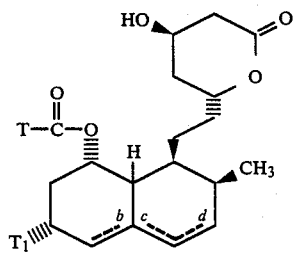

| Compound | T | T1 | b | c | d |
|---|---|---|---|---|---|
| 12 | HO—⌬(F)—C(CH₃)₂— | CH₃ | — | — | — |
| 13 | (2-HO-C₆H₄)—CH(CH₃)— | CH₃ | db | — | db |
| 14 | HO—⌬—CH₂—C(CH₃)₃ | CH₃ | — | — | — |
| 15 | (3-HO-C₆H₄)—CH₂—C(CH₃)₃ | CH₃ | db | — | db |
| 16 | CH₃O—⌬—CH₂—C(CH₃)₃ | CH₃ | — | db | — |
| 17 | HO—⌬—CH₂CH—C(CH₃)₃ (with CH₃) | H | — | — | — |

TABLE 3-continued

[Structure: decalin core with HO-substituted lactone side chain, T-C(=O)-O- ester group, T1 substituent, CH3, with positions b, c, d on the ring]

| Compound | T | T1 | b | c | d |
|---|---|---|---|---|---|
| 18 | 4-CF3-C6H4-CH2CH(CH3)-CH(CH3)- | H | db | — | — |
| 19 | 2,4-diF-C6H3-CH2CH(CH3)- | H | — | — | db |
| 20 | 4-(CH3C(=O)O)-C6H4-CH2CH(CH3)- | H | — | — | — |
| 21 | 3-(CH3SCH2)-C6H4-CH(CH3)- | H | db | — | db | db = double bond

TABLE 4

[Structure: decalin core with HO-substituted lactone side chain, T-C(=O)-O- ester, T1, T2 substituents on one ring, T3 on the other, CH3, with positions a, b, c, d]

| Compound | T | T1 | T2 | T3 | a | b | c | d |
|---|---|---|---|---|---|---|---|---|
| 22 | 4-HO-3-F-C6H3-CH2C(CH3)2- | OH | H | H | — | db | — | db |
| 23 | C6H5-CH(CH3)- | OH | H | H | — | db | — | db |
| 24 | 4-(H2NSO2)-C6H4-C(CH3)2- | OH | H | H | — | — | — | — |

TABLE 4-continued

| Compound | T | T₁ | T₂ | T₃ | a | b | c | d |
|---|---|---|---|---|---|---|---|---|
| 25 | (structure with CH₂CH₂C(CH₃)₂— group attached to phenyl with PhCO-O substituent) | — | CH₃ | OH | db | — | db | — |
| 26 | (structure with CH(CH₃)— group attached to phenyl with CH₃OCH₂ substituent) | — | H | OH | db | — | db | — |

EXAMPLE 27

Preparation of Alkali and Alkaline Earth Salts of Compound II

To a solution of the lactone from Example 1(d) (42 mg) in ethanol (2 ml) is added 1 ml of aqueous NaOH (1 equivalent). After one hour at room temperature, the mixture is taken to dryness in vacuo to yield the sodium salt of Compound II.

In like manner the potassium salt is prepared using one equivalent of potassium hydroxide, and the calcium salt using one equivalent of CaO.

EXAMPLE 28

Preparation of Methyl Ester of Compound II

To a solution of 400 mg of the lactone from Example 1(d) in 100 ml of absolute methanol is added 10 ml 0.1M sodium methoxide in absolute methanol. This solution is allowed to stand at room temperature for one hour, is then diluted with water and extracted twice with ethyl acetate; the ethyl acetate, dried over anhydrous sodium sulfate, is removed in vacuo to yield the methyl ester of Compound II.

In like manner, by the use of equivalent amounts of propanol, butanol, isobutanol, t-butanol, amyl alcohol, isoamyl alcohol, 2-dimethylaminoethanol, benzyl alcohol, phenethanol, 2-acetamidoethanol, and the like, the corresponding estes are obtained.

EXAMPLE 29

Preparation of free Hydroxy Acids

The sodium salt of the compound II from Example 27 is redissolved in 2 ml of ethanol-water (1:1) and added to 10 ml of 1N hydrochloric acid from which the hydroxy acid is extracted with ethyl acetate. The latter solvent is washed once with water, dried, and removed in vacuo with a bath temperature not exceeding 30° C. The hydroxy acid derived slowly reverts to the lactone on standing.

EXAMPLE 30

As a specific embodiment of a composition of this invention, 20 mg of the lactone from Example 1(d) is formulated with sufficient finely divided lactose to provide a total amount of 580 to 590 mg to fill a size 0 hard gelatin capsule.

What is claimed is:

1. A compound represented by the following general structural formula (I'):

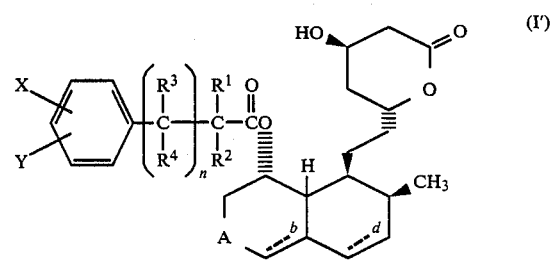

wherein:
n is 0 to 2;
$R^1$ is $C_{1-3}$alkyl;
$R_2$ is hydrogen or $C_{1-3}$alkyl;
each of the $R^3$s and $R^4$s are independently selected from hydrogen or $C_{1-3}$alkyl;
X and Y independently are hydrogen, trifluoromethyl, hydroxy, $C_{1-3}$ alkyl thiomethyl, hydroxy methyl, or aminomethyl, provided that both X and Y are not hydrogen;
A is

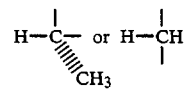

and b and d represent single bonds, or both b and d represent double bonds.

2. A compound according to claim 1 wherein:
R¹ is methyl;
X and Y independently are hydrogen, trifluoromethyl or hydroxy, provided that both X and Y are not hydrogen.

3. A compound according to claim 2 wherein:
n is 0.

4. A compound according to claim 3 wherein:
R² is methyl.

5. A compound according to claim 4 wherein:
X is hydroxy; and
Y is hydrogen or hydroxy.

6. A compound according to claim 5 which is 6(R)-[2-[8(S)-(α,α-dimethyl-4'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

7. A compound according to claim 5 which is 6(R)-[2-[8(S)-(α,α-dimethyl-3'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

8. A compound according to claim 5 which is 6(R)-[2-[8(S)-(α,α-dimethyl-4'-hydroxymethyl-phenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

9. A compound according to claim 2 wherein:
n is 1.

10. A compound according to claim 9 wherein:
R² is methyl;
R³ and R⁴ are hydrogen; and
b and d represent double bonds.

11. A compound according to claim 10 wherein:
X is hydroxy; and
Y is hydrogen or hydroxy.

12. A compound according to claim 11 which is 6(R)-[2-[8(S)-[(α,α-dimethyl-3-(4'-hydroxyphenyl)-propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

13. A compound according to claim 11 which is 6(R)-[2-[8(S)-[(α,α-dimethyl-3-(3',5'-dihydroxyphenyl)-propionyloxy]-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

14. A compound according to claim 2 wherein n is 2.

15. A hypocholesterolemic, hypolipidemic pharmaceutical composition comprising a nontoxic therapeutically effective amount of a compound of claim 1 and a pharmaceutically acceptable carrier.

16. A composition according to claim 15 wherein:
R¹ is methyl;
X and Y independently are hydrogen, trifluoromethyl, or hydroxy.

17. A composition according to claim 16 wherein:
R² is methyl; and
b and d are double bonds.

18. A composition according to claim 17 wherein:
X is hydroxy; and
Y is hydrogen or hydroxy.

19. A composition according to claim 18 wherein the therapeutically active ingredient is selected from the group consisting of:
(1) 6(R)-[2-[8(S)-(α,α-dimethyl-4'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2one;
(2) 6(R)-[2-[8(S)-(α,α-dimethyl-3'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;
(3) 6(R)-[2-[8(S)-(α,α-dimethyl-4'-hydroxymethyl-phenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one.

20. A composition according to claim 18 wherein the therapeutically active ingredient is selected from the group consisting of:
(1) 6(R)-[2-[8(S)-(α,α-dimethyl-4'-hydroxyphenylacetyloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one;
(2) 6(R)-[2-[8(S)-[α,α-dimethyl-3-(3',5'-dihydroxyphenyl)-propionyloxy]-2(S),6(R)-dimethyl-1,2,6,7,8,8a(R)-hexahydronaphthyl-1(S)]-ethyl]-4(R)-hydroxy-3,4,5,6-tetrahydro-2H-pyran-2-one.

21. A hypocholesterolemic, hypolipidemic pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and a pharmaceutically acceptable carrier.

22. A method of inhibiting cholesterol biosynthesis comprising the administration to a subject in need of such treatment a nontoxic therapeutically effective amount of a compound of claim 1.

* * * * *